United States Patent [19]
Kissinger et al.

[11] Patent Number: 5,816,256
[45] Date of Patent: Oct. 6, 1998

[54] MOVEMENT-RESPONSIVE SYSTEM FOR CONDUCTING TESTS ON FREELY-MOVING ANIMALS

[75] Inventors: Candice B. Kissinger; Curtis E. Bohs; William F. Schmidt, all of West Lafayette; Donnie A. Evans, Dayton, all of Ind.

[73] Assignee: Bioanalytical Systems, Inc., Indianapolis, Ind.

[21] Appl. No.: 839,299

[22] Filed: Apr. 17, 1997

[51] Int. Cl.[6] .............................. A61B 19/00; A01K 1/03
[52] U.S. Cl. ............................. 128/897; 119/421
[58] Field of Search ........................ 600/300; 128/897, 128/898; 119/417, 421

[56] References Cited

U.S. PATENT DOCUMENTS

| | | |
|---|---|---|
| 3,897,751 | 8/1975 | Gullino et al. . |
| 3,999,519 | 12/1976 | Rodemeyer . |
| 4,284,034 | 8/1981 | Belew . |
| 5,345,943 | 9/1994 | Hargreaves et al. . |
| 5,419,312 | 5/1995 | Arenberg et al. . |
| 5,558,073 | 9/1996 | Pomeranz et al. . |
| 5,564,434 | 10/1996 | Halperin et al. . |
| 5,598,847 | 2/1997 | Renger . |

OTHER PUBLICATIONS

M. A. Parada, et al, Journal of Neuroscience Methods 60, Jan. 12, 1995, 133–139.
H. Matsumura, et al., Journal of Neuroscience Methods 57, Jun. 24, 1994, 145–149.

Primary Examiner—Jennifer Bahr
Assistant Examiner—Eric F. Winakur
Attorney, Agent, or Firm—Ice Miller Donadio & Ryan; Doreen J. Gridley

[57] ABSTRACT

A movement-responsive system for conducting tests on freely-moving animals is disclosed. The invention includes a container for housing the animal, a mechanism for rotating the cage in response to rotational movement of the animal, and one or more test leads connected to the animal for performance of biomedical tests such as infusion, in vivo ultrafiltration, laser-doppler monitoring of blood flow, electrical stimulation, and in vivo microdialysis. The container is caused to rotate in the opposite (counter-rotation) direction of the sensed direction of rotation of the animal so that the one or more test leads do not become entangled, twisted, disconnected, or clamped. The rotating mechanism includes a simple, reliable sensor assembly including a pair of strategically placed, close-ended limit detectors which are activated by a triggering element, which is also a part of the sensor assembly. The sensor assembly is mounted on a counter-balanced arm which is responsive to upward and downward movements of the animal. No complex control system is required for the present invention, yet adjustment of the sensitivity of the rotating mechanism is easy to accomplish and may be performed by the average user of the apparatus. Further, the leads may all be continuous, thereby eliminating problems caused by the use of liquid swivels with independently rotating halves, or by commutator connectors.

21 Claims, 6 Drawing Sheets

MOVEMENT-RESPONSIVE SYSTEM FOR CONDUCTING TESTS ON FREELY-MOVING ANIMALS

FIELD OF THE INVENTION

This invention relates to an apparatus for use in biomedical research, and, in particular, to a system for conducting infusions, electrophysiology, ultrafiltration, microdialysis, electrochemistry, optical fiber transmission and behavioral monitoring in conscious, freely-moving animals.

BACKGROUND OF THE INVENTION

Working with conscious animals is a requirement of important biomedical research techniques such as infusion, in vivo microdialysis, in vivo ultrafiltration, in vivo electrochemistry, biosensors and electrophysiology. All of these methods study the functioning of living organs such as the brain, heart, circulatory system, muscles, etc. They also involve connections between external devices such as syringe pumps, fraction collectors, electrometers, vacuum sources, light sources, and potentiostats to implants in the animal's body such as infusion cannula, ultrafiltration probes, microdialysis probes, or electrodes. The means of connection is typically a length of flexible, hollow, plastic tubing, a flexible wire, or an optical fiber.

Frequently, in the prior art, the connection of one or more lines of tubing for conveyance of fluids in such tests involves the use of a liquid swivel, or, for electric or optical leads, the use of a swivel-commutator (such as an electrocannular device). In general, a portion of the lead is connected to the top of the swivel which is mounted on a support above the animal, while an additional portion of the lead is connected from the implant on the animal to the underside of the swivel. Liquid swivels are designed so that the top and bottom half rotate independently and an internal seal connects the two halves. When the connection is electrical or optical, a form of commutator is required. For liquid swivels and swivel commutators, the lead is discontinuous, i.e., it is somehow "split" at the swivel, so that the bottom half of the lead may be required to rotate with respect to the top half of the lead.

Liquid swivels are frequently unreliable. Further difficulty in their employment results when there is a need to connect more than one tubing line, as in microdialysis. Multi-channel liquid swivels typically use concentric cannulae with concentric, complex seals separating each channel from the next. The seals wear easily when exposed to salty, physiological solutions. When they leak, cross-channel contamination is a common occurrence. Use of liquid swivels is also difficult when an electric or optical line (lead) is to be connected to the animal, for such an electric or optical lead requires the addition of a commutator to maintain contact with leads attached to the animal. Although the swivel and commutator can accommodate rotation of the respective leads, the leads, or a portion thereof, can become entangled when the leads rotate with respect to each other.

The use of a liquid swivel undesirably adds additional volume to a fluid path. For example, connecting tubing for microdialysis typically has an internal diameter of 0.12 mm. A length of 10 cm of such tubing contains a volume of approx. 1.2 $\mu$L of fluid. A two channel liquid swivel, such as the stainless steel model available from Instech Laboratories of Plymouth Meeting, Pa., has a dead volume of 1.4 $\mu$L for the center channel and 18.5 $\mu$L for the side channel. Thus, when such a swivel is used, it takes more time to transfer fluid the same distance due to the dead volumes of the channels. Consider a situation where the distance between the animal and a device such as a fraction collector is 30 cm, where the fluid travels at a rate of 2 $\mu$L per minute, and the height of the swivel is 5 cm. The volume in 30 cm of tubing is 3.6 $\mu$L, and it would take 1.8 minutes for the fluid to travel from one end to the other of this 30 cm tubing. A 5 cm long swivel and 25 cm of tubing would occupy the same distance, but the volume of this combination (using the center swivel channel of the Instech Laboratories tubing) would increase to 4.4 $\mu$L, and, thus, it would take 2.2 minutes for fluid to traverse this combination of tubing and swivel. If the side channel of the swivel was used, the volume would be 21.5 $\mu$L, and time for traversing the tubing and swivel would increase to 10.7 minutes.

The use of liquid swivels is common, as described above. The article "Triple electrical channels on a triple fluid swivel and its use to monitor intracranial temperature with a thermocouple" by Parada et al., Journal of Neuroscience Methods, Vol. 60 (1995), pg. 133–139, describes a complex liquid swivel which deals with the aforementioned limitations in fluid channels by creating an extremely complex device. It is desirable to avoid such a complex system, and to avoid the use of liquid swivels while permitting for free movement of the animal.

Another shortcoming of swivel systems relates to tracking the behavior of the freely-moving animal. Rotational behavior in laboratory rodents is well-established as an indicator of neurochemical changes occurring in the animal. Tracking of the clockwise or counterclockwise preference of the animal and the frequency of such rotation are valuable data not available with the prior art liquid swivel systems. It is therefore desirable to provide a system which not only permits for rotation of the animal, but also which is capable of tracking the rotational preference and frequency of rotation of such rotation for identification of behavioral changes occurring during testing.

As previously stated, most prior art systems which permit for rotation of the animal use electrical and/or optical commutators for electrical or optical leads. Although such commutators accommodate rotation of the animal, they frequently introduce "noise" or other interference which may contaminate the signal. Such contamination is undesirable as it may result in inaccurate results. Further, if multiple electrical and/or optical leads are connected to a commutator, cross-talk (noise and/or interference) can result to result in erroneous signals across such leads.

The use of liquid swivels and commutators also results in additional manufacturing costs and in unwanted repair costs. It is preferred to avoid the use of swivels to avoid the extra expense thereof in manufacture. Also, because the swivels naturally wear out during the course of normal use, continual repair or replacement of the swivel is required.

An apparatus for infusion in a freely-moving animal is disclosed in U.S. Pat. No. 3,897,751, Gullino et al. The apparatus of Gullino et al. utilizes a continuous catheter to infuse the animal and permits for movement of the animal by threading the catheter between the walls of the cage and an elevated cover. Gullino et al. does not permit for rotation of the animal, however. In fact, if such rotation were to occur, because the ends of the catheter are affixed, stress is applied to the catheter. Such rotational stress could result in harm to the animal or may disconnect or impair the connection of the catheter to the source of fluid. Therefore, it is desired to provide an apparatus for infusion in a freely-moving animal which permits for the rotational movement of the animal while employing continuous leads which does not result in harm to the animal or disconnection or impairment of the connection of the lead to its source.

Another apparatus for conducting tests on freely-moving animals is described in a scientific article entitled "A novel apparatus that permits multiple routes for infusions and body-fluid collections in a freely-moving animal", Matsumura et al., Journal of Neuroscience Methods, Vol. 57 (1995), pg. 145–149. Matsumura et al. does disclose a movement-responsive apparatus which permits for rotation of the animal by rotating the floor of the cage housing the animal. Specifically, in the disclosed apparatus, multiple fluid lines are passed through the center of a device mounted to a fixed support above a cylindrical chamber. The animal is tethered to this device by the electrical lines. The electrical lines are connected through a slip-ring commutator on the exterior of the device. This type of connection means that the top and bottom half of the device rotated independently, like a swivel. The floor of the cylinder portion of the cage is moved in response to the animal's movement while the walls of the cage are immobile.

The apparatus of Matsumura et al. has several shortcomings, however. For example, electrical connection is made in Matsumura et al. through a commutator requiring electrical contacts and connections. A continuous wire (lead) is preferred to avoid the possibility of disconnection and to prevent introduction of electrical noise through the contacts and connections which may lead to erroneous or inaccurate results through the lead. This concept also applies to an optical fiber lead, which is not disclosed in Matsumura et al. The invention of Matsumura et al. also permits full rotation of the animal through three, or more, complete 360 turns before responding to the animal's movement with counter-rotation. This movement can create undesirable twisting and stress on the leads connected to the animal. There is no physical limit to continuous rotation of the sensor assembly described by Matsumura et al. since an encoded plate passes freely through open-ended sensors. A complex, expensive microcomputer controller is required to interpret direction and magnitude of rotation and to cause the stepping motor to rotate the cage floor. It is desirable to provide a simple electrical circuit which does not employ such a microcomputer to reduce manufacturing and repair costs, to improve reliability of the controller, and to avoid the need for programming expertise. Such a programming requirement is also necessary to adjust the sensitivity of the sensor system to rotation of the animal housed in the cage. It is desirable to provide a sensor system which does not require programming for sensitivity adjustment. Not only may such programming be complex, but the use of the microcomputer necessitates that the sensitivity adjustment be made by the manufacturer or its qualified representative by a change in programming, and does not permit for easy sensitivity adjustment in the laboratory. Thus, it is preferred that the sensor system of the apparatus permit the technician in the laboratory, or other qualified personnel, to adjust the sensor system's sensitivity in the laboratory without requiring programming of a microcomputer. Further, despite employment of a microcomputer, the apparatus of Matsumura et al. does not track rotational behavior of the animal—a valuable indicator of neurochemical changes occurring in the animal during testing.

In the apparatus of Matsumura et al., the sensor system is triggered by movement of the electrical lead(s) connected to the animal and to the electrical commutator. Specifically, tension must be placed on the lead(s) to cause rotation of a tube whose movement is sensed. The use of the electrical lead in this circumstance is highly undesirable as it places stress on the animal and/or the connection of the lead to the commutator. Therefore, it is desirable to provide a sensor apparatus which does not place stress on any of the leads—including the end of the lead connected to the animal and the end of the lead connected to a test apparatus or source, such as fluid or light, for example.

In addition to these shortcomings, it is desirable to provide a movement-responsive testing apparatus which rotates the entire cage rather than just the cage floor as in Matsumura et al. Rotation of the entire cage eliminates the possibility that bedding material in the cage or part of the animal is caught in the interface between the stationary walls and the rotating floor of the cage. Matsumura et al. notes that animals in their device were observed to hold onto a food container with their forelegs and walk with their back legs to continue eating while the floor was rotating. Therefore, rotation of the entire cage can facilitate a more stable environment for the animal, and can permit for devices, such as water bottles and food supplies, to remain in a fixed position from the animal's perspective.

Accordingly, it is an object of the present invention is to avoid the use of a liquid swivel and/or commutators in a conscious animal monitoring system to thereby result in the following advantages over the prior art:

Eliminate the need to compensate for and accommodate the extra system volume of a liquid swivel;

Impose no restrictions on the number or combination of electrical, fluid or optical channels employed in the system;

Impose no restrictions on the relative placement of different types of channels (e.g. electrical and fluid) used in the same monitoring system;

Eliminate the need to compensate for and accommodate the extra liquid travel time between the implant and the external device (pump, fraction collector, etc.) caused by a liquid swivel;

Avoid cross-contamination between channels that result in a liquid swivel which is capable of handling multiple fluids;

Eliminate the potential for cross-talk between electrical or optical channels on a commutator, and for noise and/or interference caused by use of a commutator;

Avoid the extra expense from continual replacement or repair of swivels or commutators which naturally wear out during the course of normal use.

It is another object of the present invention to provide a movement-responsive system which tracks rotational behavior of the animal.

It is yet another object of the present invention to provide a system which does not require leads subject to rotational forces to be affixed to either the animal or the source or device to which the lead is connected to thereby avoid potential harm to the animal or to disconnection or impairment of the connection of the lead to the animal or to the source or device.

It is still another object of the present invention to provide a sensor system which is inexpensive to manufacture and which is highly reliable during operation.

It is another object of the present invention to provide a sensor system having the capability to be adjusted for sensitivity to the animal's movement, with such adjustment being easy to perform in the laboratory environment.

Also, it is yet another object of the present invention to provide a movement-responsive system in which the entire cage housing the animal is rotated to stabilize the animal's environment and to avoid the possibility that bedding or other materials or the animal itself may become caught between portions of the cage that rotate and portions that do not rotate.

Further, it is still another object of the present invention to provide a movement-responsive system which can be utilized for a myriad of biomedical tests performed on freely-moving animals, including but not limited to infusion, electrophysiology, blood monitoring, ultrafiltration, microdialysis, electrochemistry, optical fiber transmission, and behavioral monitoring, and which permits for more than one such tests to be performed concurrently.

Another object of the present invention is to provide a testing apparatus which does not result in undesirable change in the animal's behavior as results from some of the prior art systems.

An additional object of the present invention is to accommodate both the rotational and vertical movements of an experimental animal by use of a rotational sensor mounted on a counter-balanced arm and tether assembly which keeps leads out of the animal's reach, and reduces animal stress by minimizing collar tension.

It is another object of the present invention to provide a system with these and other capabilities and features which is inexpensive to manufacture, repair and maintain.

SUMMARY OF THE INVENTION

The present invention comprises an apparatus for performing at least one biomedical test on a freely-moving animal. It is a reliable movement-responsive system which rotates the cage in response to rotational movement of the animal in the cage to avoid entanglement, crimping, disconnecting, or twisting the leads that are connected to the animal for testing purposes. In one embodiment, the apparatus comprises a cage for housing the animal, a means for rotating the cage in response to rotational movement of the animal, and at least one lead for performance of at least one biomedical test on the animal.

The rotating means includes a sensing means which includes first and second close-ended, limit detectors which are of the type to be activated by an interruption or reflection of a light beam, a magnetic field, a radioactive field, a flow of gas or liquid, or a simple contact with a microswitch, pressure sensitive button, magnet, electrical contact wire, or other such mechanism. The first and second limit detectors are positioned at a predetermined position with respect to each other, with this position being adjustable to adjust sensitivity of the apparatus. The sensing means also includes a triggering element having at least a portion thereof capable of activating the limit detectors. Since the limit detectors are closed on one end, deactivation of an activated limit detector can only occur by reversal of the animal's movement.

The rotating means further includes a means for driving rotation of the container. The driving means is electrically connected to the first and second limit detectors, such that activation of the first detector causes the driving means to rotate the container in a clockwise direction and activation of the second detector causes the driving means to rotate the container in a counterclockwise direction. In addition to the sensing means, rotating element and driving means, the rotating means includes a tether line for tethering the animal to the sensing means to cause rotation of the rotating element upon rotational movement of the animal.

The apparatus of the present invention further includes at least one test lead for performance of at least one biomedical test. The lead has a first end for connection to the animal and a second end for connection to a device external to both the animal and the containment system. During operation, rotational movement of the animal causes the rotating element of the rotating means to trigger either the first or second limit detectors to thereby result in counter-rotation of the container. In addition, the rotating and sensing means are mounted on a lever arm which responds to upward and downward movement of the animal through a counter-balanced weight which pulls the rotating and sensing means, and all associated leads away from the animal (during upward movement) and with the animal (during downward movement).

Other devices used to contain animals during infusions, microdialysis, blood flow monitoring, or electrical recording are complex and/or unreliable, and have one or more of the shortcomings discussed herein. The present invention offers a simple and reliable means of connecting a device implanted in or attached to an animal to an external controlling or monitoring device located at a distance from the animal which permits the animal to move freely during such biomedical testing. Some of the advantages of the present invention over the prior art are summarized as follows:

Connecting tubing, optical fibers, and wires (collectively referred to herein as "leads") are not broken. They remain as a single, unbroken piece connecting the implanted device to the external device.

Multiple leads can be used with no risk of cross-contamination since they are not joined or connected through a swivel, commutator or other junction. Further, for electrical and optical leads the risk of noise or interference from connections is eliminated.

Electrical wires and/or optical fibers can be used at the same time as tubing lines filled with fluid.

The sensor assembly differentiates between clockwise and counterclockwise rotation by the animal and moves the animal, in its cage, in the opposite direction.

Signals from the sensor assembly can be recorded by a simple strip chart recorder or device such as a computer. These signals record the overall activity of the animal and its clockwise and/or counterclockwise movement. Further, the system is not likely to cause behavioral changes in the animal.

The sensor assembly is mounted on a counter-balanced arm so that slack in tubing or wires is taken up and away from the animal. This also creates less stress for the animal since the system responds to its vertical movements.

The container can be a single piece of plastic formed into a round-bottomed bowl which prevents contact between the implant on the animal and cage walls The entire container, including food and water dispensers and the animal it contains, is rotated in response to animal movement.

The container can be covered to remove visual cues to movement which are external to the container. Various covers can also be used to test behavioral responses to visual stimuli.

DETAILED DESCRIPTION

Figure 1:
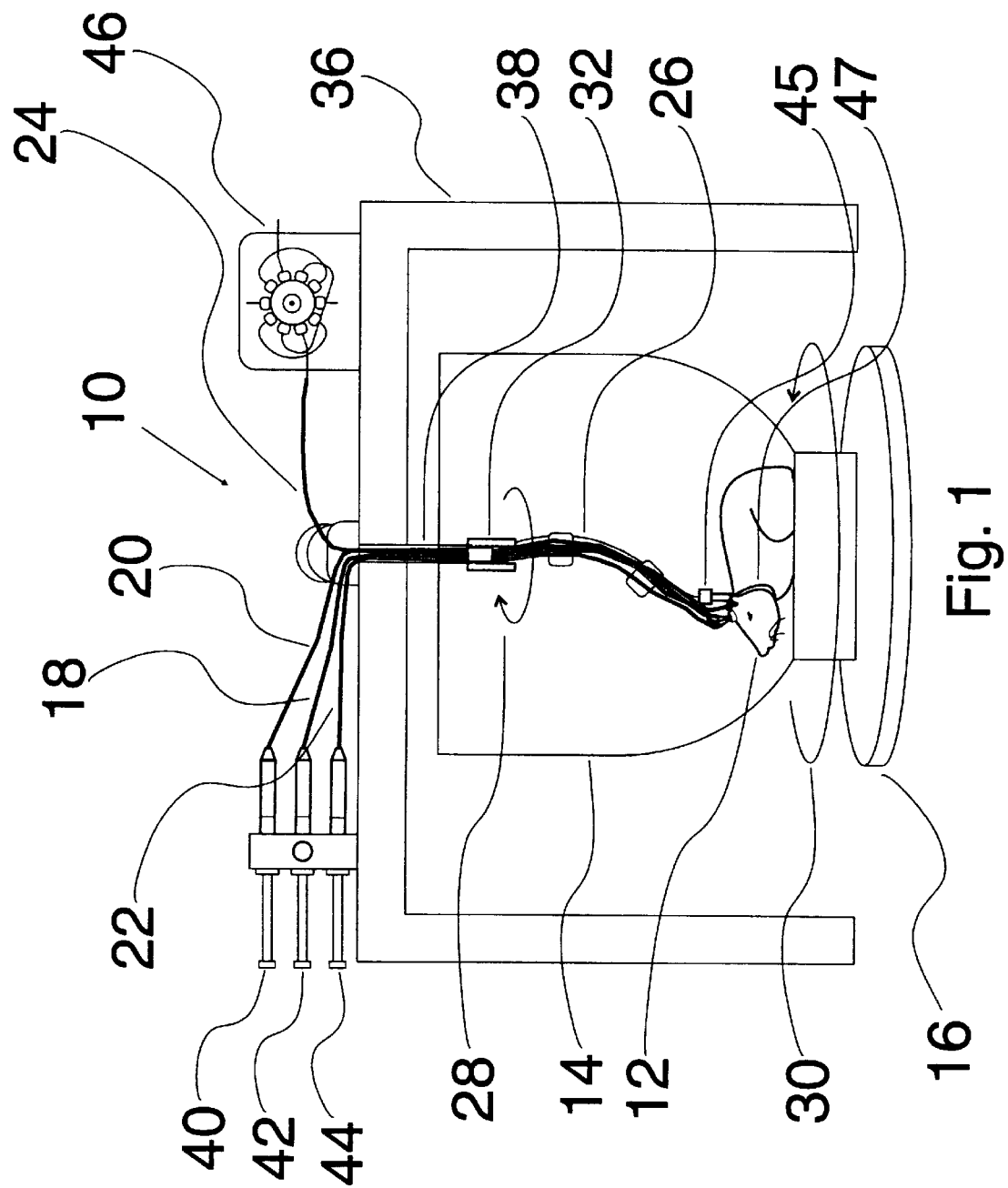
FIG. 1 shows a side view of one embodiment of the apparatus of the present invention.

Referring now to FIG. 1, there is shown a side view of one embodiment of the apparatus of the present invention. Specifically, in this embodiment, movement-responsive test system 10 is capable of performing biomedical tests on animal 12, which in this embodiment is a laboratory rat. Animal 12 is housed within cage or bowl 14 during performance of the biomedical test(s). Cage 14 is more thoroughly described in association with FIG. 3 and FIG. 4 hereof, and is connected to powered turntable 16 as is described in association with FIG. 2 hereof. Animal 12 is connected to test leads 18, 20, 22 and 24 and to tether line 26 as is described in greater detail herein.

The primary objective of system 10 is to provide an apparatus which is responsive to the rotational movement of animal 12 during biomedical testing. More specifically, if animal 12 rotates in the direction indicated by animal movement arrow 28, system 10 causes turntable 16 and cage 14 to rotate in the direction indicated by cage movement arrow 30. Similarly, if animal 12 were to rotate in a direction opposite that of animal movement arrow 28, system 10 causes turntable 16 and cage 14 to rotate opposite the direction indicated by cage movement arrow 30. In other words, system 10 causes cage 14 to rotate in the counter-rotation direction of the detected direction of rotation of animal 12. In this manner, test leads 18, 20, 22, and 24 and tether line 26 do not become twisted or entangled upon rotation of animal 12.

To accomplish this objective, system 10 includes a means for rotating cage 14 in response to rotational movement of the animal, including sensor assembly 32 for sensing movement of the animal, a means for driving rotation of cage 14 in the appropriate counter-rotational direction (see motor 34 on FIG. 2, FIG. 4, and FIG. 5), and tether line 26 for connecting animal 12 to sensor assembly 32. Sensor assembly 32 is positioned and suspended above animal 12 in cage 14 by a support means comprising support table 36 having counterbalanced arm 38 pivotally mounted thereon. The use of counterbalanced arm 38 is desirable to take up slack in and to keep leads 18, 20, 22, and 24 and tether line 26 out of the animal's reach and yet allow the animal flexibility of vertical movement without placing unwanted stress on leads 18, 20, 22 and 24 or tether line 26.

In the embodiment of FIG. 1, first lead 18, second lead 20, and third lead 22 all comprise fluid tubing implanted in the head of animal 12 at one end. The other ends of first, second and third leads 18, 20, and 22, extend through sensor assembly 32 (see FIG. 4) and are connected to first, second and third syringe pumps 40, 42, and 44, respectively, for delivery of fluids to animal 12. Fourth lead 24, also tubing, is also implanted at one end in the head of animal 12, and is connected to electrically-activated injection valve 46 at its other end for collection of fluid from a probe implanted in animal 12. This fluid would subsequently be injected into a liquid chromatography or mass spectrometry system for analysis. It is important to note that the present invention permits for each lead 18, 20, 22 and 24 to be continuous, i.e., to have no breaks or seals therein.

Figure 4:
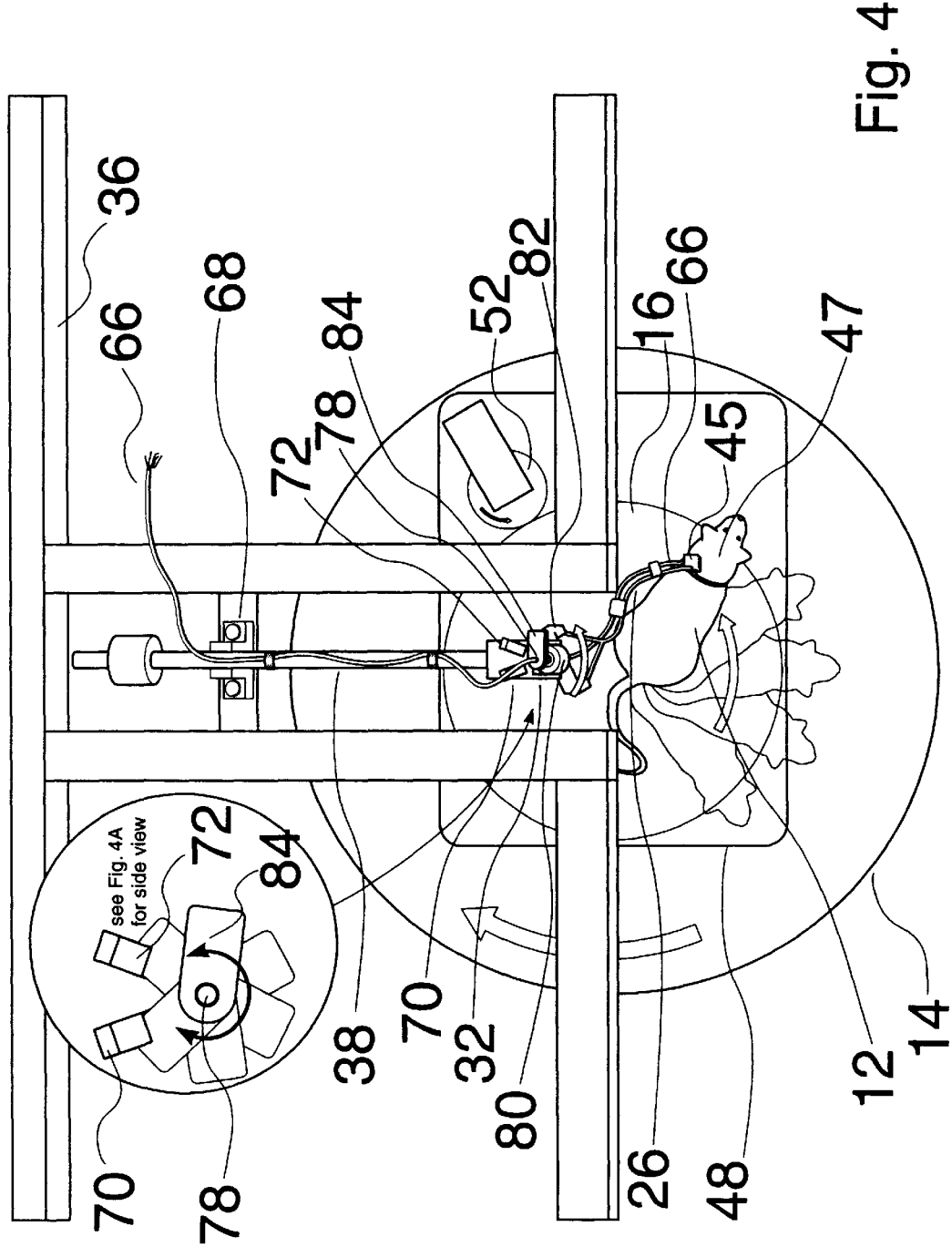
FIG. 4 shows a top view of the embodiment of the apparatus of the present invention illustrated in FIG. 1, except that all leads are gathered in a single bundle.

One end of tether line 26 is attached by means of a clamp 45 to animal 12 by collar 47. Collar 47 is essentially a belt which is non-invasively fastened about the neck of animal 12. The other end of tether line 26 is connected to sensor assembly 32 as shown in FIG. 4.

Also contemplated to be within the scope of the invention are leads which comprise electric lines for the receipt or transmission of electric signals, and optic fibers for the receipt or transmission of light signals. Such lines are illustrated in the bundle shown in FIG. 4. Also, tether line 26 may be a wire, spring, cable and the like and be within the scope of the invention. Further, cage 14 is essentially a container which restricts the animal's movement during test. Platforms or other enclosures are envisioned to be within the scope of the invention.

Figure 2:
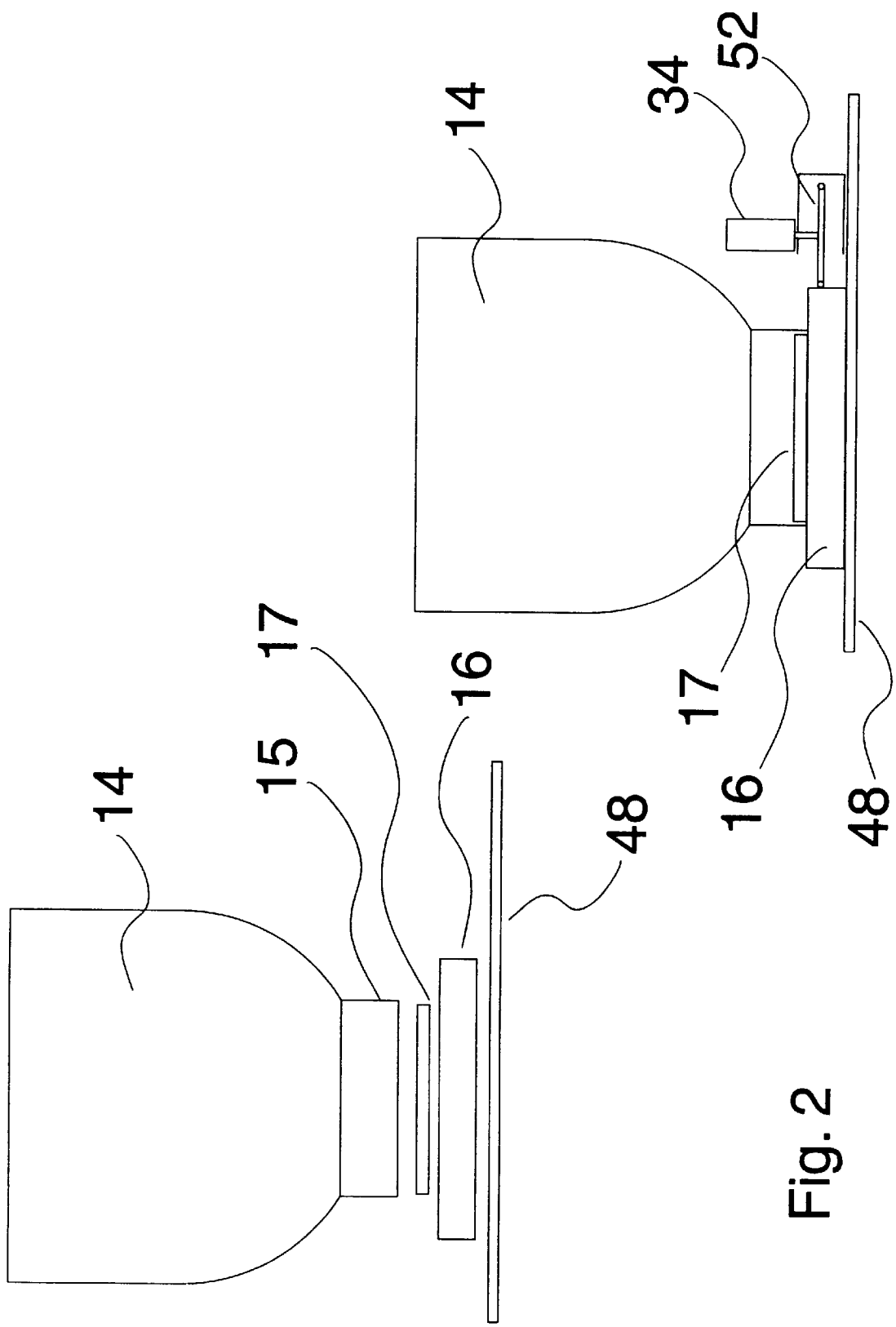
FIG. 2 shows two side views of one embodiment of the cage of the present invention, both disassembled and connected to the turntable and the electric motor for driving the turntable.

FIG. 2 shows two side views of one embodiment of the cage of the present invention, both disassembled and connected to the turntable and the electric motor for driving the turntable. Bowl 14 rests on turntable 16 as illustrated. Specifically, bowl 14 is a round bottom bowl, and may be comprised of translucent material, such as Plexiglas. To permit bowl 14 to stand and be stable, affixed, such as by glue, to the bottom exterior surface of bowl 14 is ring or bowl base 15. Bowl base 15 may also be comprised of a material such as Plexiglas. Rotatable turntable 16 is placed on, and rotates with respect to, surface 48. To keep bowl 14 in contact with turntable 16 during rotation, in this embodiment, plate 17 is attached to turntable 16. Plate 17 is sized to contact the interior circumference surface of bowl base 15 to hold bowl 14 in place. Drive wheel 52 of motor 34 engages turntable 16 to cause turntable 16, plate 17, bowl base 15, and cage 14 to rotate simultaneously. In this embodiment, motor 34 may be any reversible 12-volt DC motor, for example, and turntable 16 may be any suitably sized turntable ranging from the types used in phonographs to the types used for household kitchen cabinets.

It will be appreciated by those of skill in the art that the combination of the lo drive mechanism (motor 34 and turntable 16) with cage 14 permits for easy separation of cage 14 from the rest of system 10. Further, removal of collar 47 and/or clamp 45 from animal 12 facilitates removal of both animal 12 and cage 14 from system 10 as may be desired for cleaning of cage 14 or removal of animal 12 from connection to the system.

It will also be appreciated that rotation of the entire cage 14 is advantageous over an arrangement in which only the floor of the cage rotates. Rotating the cage and its contents at the same time as the animal makes this arrangement less disturbing to the animal as it would not appear to the animal that its food and water dispensers are rotating away from the animal as would be caused by rotation of only the cage floor. By rotating the entire cage 14, water and food attached to the walls of cage 14 also rotate. Thus, the animal is not likely to learn behavior to compensate for the rotation of the floor only as in the prior art. It is undesirable to modify the animal's behavior during testing. Also, a more stable environment is created for animal 12 and the possibility that bedding or other materials in cage 14 or animal 12 itself will become caught between portions of a cage that rotate and portions that do not rotate is eliminated with the present invention.

Figure 3:
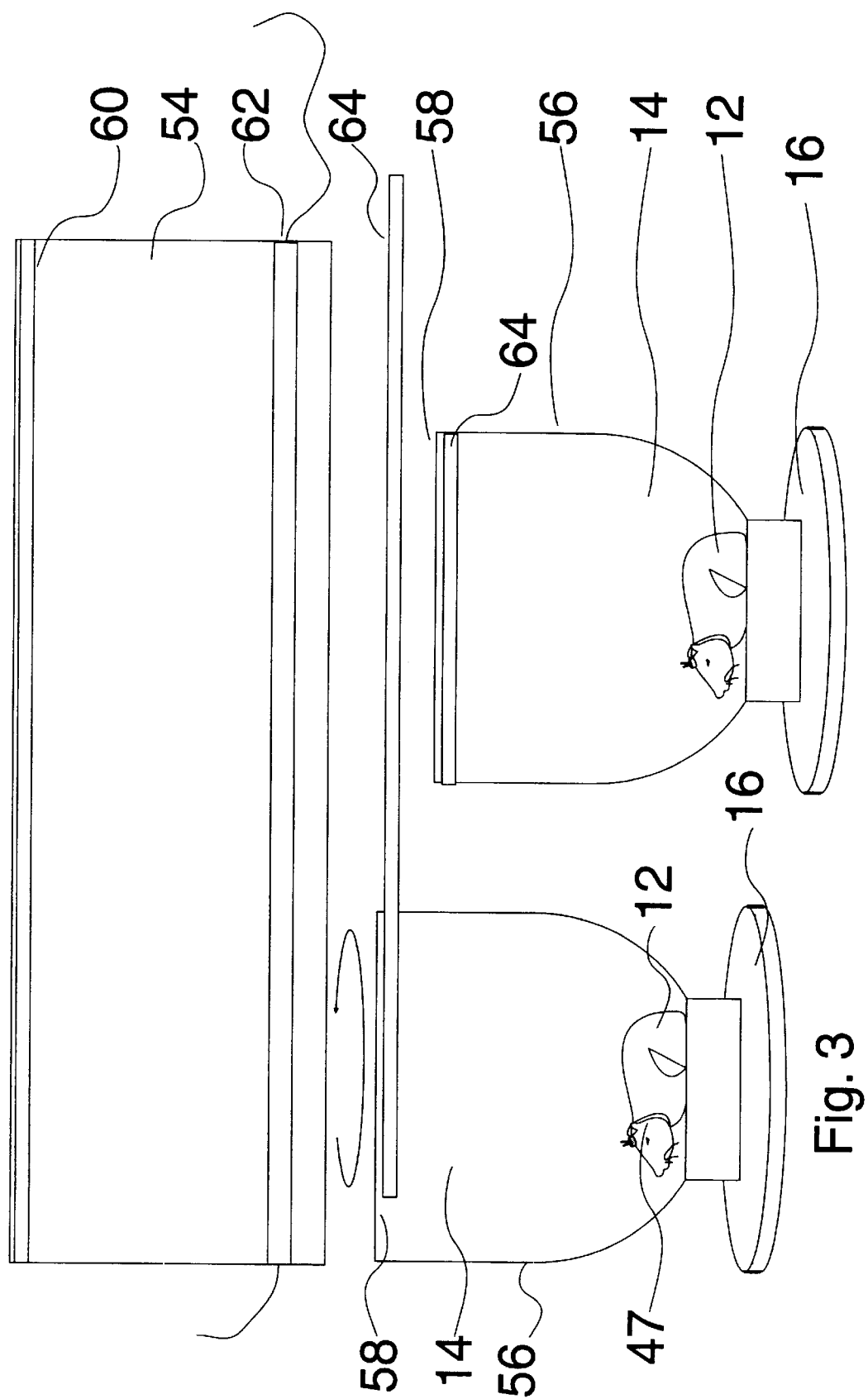
FIG. 3 shows a side view of one embodiment of the cage and cage cover of the present invention.

Referring now to FIG. 3, there is shown a side view of one embodiment of the cage and cage cover of the present invention. As in the embodiment of FIG. 1, cage 14 of this embodiment comprises a round-bottom bowl made of translucent or transparent material such as plastic, Plexiglas, or glass. The shape of bowl 14 prevents casual contact between leads 18, 20, 22 and 24 and tether line 26 and the interior walls of bowl 14. The use of such materials permits an observer to view animal 12 while animal 12 is in cage 14 or inserted into or removed from cage 14. It may be desirable, however, for some biomedical tests, to cover cage 14 to reduce the sensation of movement experienced by the animal 12 during rotation of cage 14 by eliminating stationary visual cues residing outside cage 14.

To accomplish this objective without requiring cage 14 to be made of a non-translucent material, cage cover 54 is provided for removable connection to cage 14. Cover 54 is made of a non-translucent, flexible material, such as dark colored cloth or flexible plastic. Cover 54 is rectangular in shape and is of a length sufficient to cover the top edge 58 of cage 14. Attached near one edge of the length of cover 54 is at least one fastener 60, which in this embodiment comprises a strip of the hooked portion of a VELCRO™ fastener running the entire length of cover 54. Near the opposing edge of cover 54 is a drawstring fastener 62.

Attached to bowl 14 near its top edge 58 is at least one mating fastener 64, which in this embodiment comprises the loop portion of a VELCRO™ fastener. Mating fastener 64 is positioned for fastening to fastener 60 of cover 54 so that when cover 54 is so fastened to bowl 14, cover 54 substantially covers the entire exterior surface walls 56 of bowl 14 around the entire circumference thereof. To engage cover 54 against exterior surface walls 56 at the bottom of bowl 14, drawstring fastener 62 may be drawn and tied.

Other types of fasteners other than a single length of VELCRO™ fastening material or a drawstring are contemplated to be within the scope of the invention. Other fasteners may include snaps, rivets, magnetic strips, zippers, elastic seams, or adhesive, for example. Further, cover 54 may be of a different shape than the rectangular shape shown in FIG. 3. It is possible, for example, to shape cover 54 so that no drawstring fastener 62 is required.

FIG. 4 shows a top view of the embodiment of the apparatus of the present invention illustrated in FIG. 1, except that all leads are gathered together in a single bundle. Specifically, leads including fluid tubing, electric lines and optic fibers are bundled together in lead bundle 66. The external devices to which these leads are connected are not illustrated in this FIG. 4. As shown in this FIG. 4, sensor assembly 32 is connected to counterbalanced arm 38. Counterbalanced arm 38 is pivotably connected to support table 36 at pivot 68, thus permitting sensor assembly 32 to move up and down with respect to cage 14 and turntable 16. As previously stated, this support means for sensor assembly 32 takes up slack in lead bundle 66 and tether line 26, and keeps lead bundle 66 and tether line 26 above and out of the reach of animal 12, while permitting animal 12 to move vertically within cage 14 without placing undesired stress on lead bundle 66, tether line 26, or the ends thereof connected to animal 12 or to the external device (such as syringe pumps 40, 42 and 44 and injector 46 shown in FIG. 1).

Sensor assembly 32 comprises first and second limit detectors in the form of optical sensors 70 and 72, respectively, connected to counterbalancing arm 38. First and second optical sensors are of the type which emanate a light beam in the direction of paths 71 and 73, respectively (see FIG. 4A), and which are activated upon interruption of the respective light beam. In this embodiment, first and second limit detectors 70 and 72 are LED type opto-interrupters, and may be Motorola Corp.'s model no. H21, for example. Sensors 70 and 72 are set at a predetermined angle with respect to each other, the significance of which is discussed later herein. The angle is a rotational measurement between sensors 70 and 72 with respect to the triggering element (second bracket 84) as described below. Further, first and second limit detectors 70 and 72 are close-ended, each having stop 87 and 89, respectively, which are discussed in greater detail herein in association with FIG. 4A.

Sensor assembly 32 also comprises hollow tube 78 within ball bearing 80 which is attached to arm 38 to permit hollow tube 78 to rotate while attached to counterbalancing arm 38 and in the same direction as animal 12 rotates, whether clockwise or counterclockwise. Lead bundle 66 passes through hollow tube 78 in the center of ball bearing 80 so that rotation of hollow tube 78 does not result in rotation of lead bundle 66 or the leads within lead bundle 66.

The center of rotation of hollow tube 78 is strategically positioned in this embodiment. Specifically, the axis of rotation of hollow tube 78 permits for intersection by second bracket 84 of both light beams of first and second optical sensors 70 and 72 for activation of the respective sensor 70 or 72 as described herein.

Attached at one end of hollow tube 78 is first bracket 82, and attached at the other end of hollow tube 78 is second bracket 84. Thus, first and second brackets 82 and 84 and hollow tube 78 all rotate together when a rotational force is applied thereto to cause hollow tube 78 to rotate within ball bearing 80. First bracket 82 is positioned so that no portion thereof triggers either beam emanating from first and second sensors 70 and 72, and, in this embodiment is located below limit detectors 70 and 72. Tether line 26 is connected to first bracket 82 such that rotational movement of animal 12 causes rotation of first bracket 82, hollow tube 78, and second bracket 84.

Figure 4A:
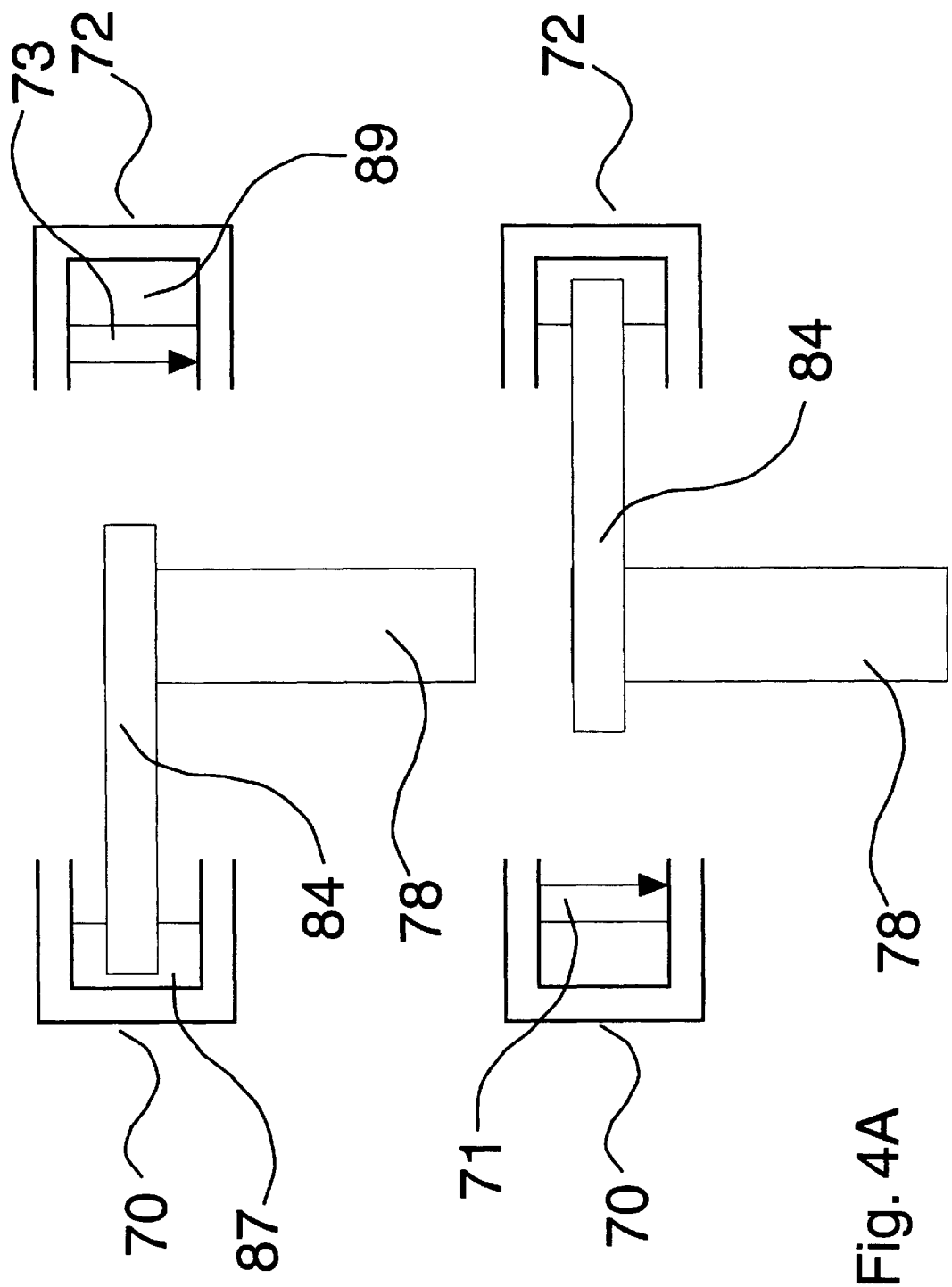
FIG. 4A shows side views of the limit detectors and triggering element of the embodiment of FIG. 4 to illustrate activation of the limit detectors.

As shown in FIG. 4A, second bracket 84 has a portion thereof which is capable of intersecting light beams emanating from first and second sensors 70 and 72 in paths 71 and 73, respectively. Specifically, second bracket 84 is a bracket with the first leg of second bracket 84 positioned so as not to intersect light beams of sensors 70 and 72. The axis of rotation of hollow tube 78, first bracket 82 and second bracket 84 extends through the first leg. The second leg has at least a portion thereof capable of intersecting the light beams of sensors 70 and 72 at or near the positions shown in FIG. 4A. In this manner, upon rotation of the second bracket 84, the second leg of second bracket 84 interrupts the light beams emanating from first and second sensors 70 and 72 at various points—one point for each light beam.

As shown in FIG. 4A, by virtue of the fact that first sensor 70 includes first stop 87 and second sensor 72 includes second stop 89, first and second sensors 70 and 72 are "close-ended". The second leg of second bracket 84 is stopped by the respective stop means 87 or 89 of sensors 70 or 72 so that second bracket 84 cannot rotate through the U-shaped interior of sensors 70 and 72. Thus, first and second sensors 70 and 72 are either activated or deactivated, and when a close-ended limit detector, such as sensors 70 and 72 are activated, it cannot be deactivated except by reversal of the rotational motion of second bracket 84 (and hence reversal of the rotational movement of animal 12). When a close-ended limit detector is deactivated, it cannot be activated until second bracket 84 is rotated, as by rotation of animal 12, to cause second bracket 84 to trigger the limit detector.

The use of opto-interrupter sensors disclosed in this embodiment represents one of many possible "limit detectors" which can be used in the present invention and are contemplated to be part of the present invention. The limit detector can be activated by an interruption or reflection of a light beam, a magnetic field, a radioactive field, a flow of air or liquid, or a simple contact with a microswitch, pressure sensitive button, magnet, electrical contact wire, or other mechanism. Thus, "triggering elements" other than the rotating element of this embodiment are also contemplated to be within the scope of the present invention. As previously stated, the limit detectors are to be close-ended, and the triggering element must be such that it activates the limit detectors in response to rotational movement of the animal. Thus, the triggering element may be rotational, such as second bracket 84, or may be any other mechanism appropriate to activate the limit detector, including but not limited to a linearly moving device. For example, the limit detectors may be limit switches activated by a triggering element which comprises linearly-moving markers strategically located on a lead screw. When triggering element is not rotational, the rotational movement of animal 12 through tether 26 must be connected, by means well known in the art to the non-rotational movement of the triggering element. The key is that the sensor, also referred to herein as a "limit detector", is close-ended and thus results in simple electronic control as is hereinafter described.

Figure 5:
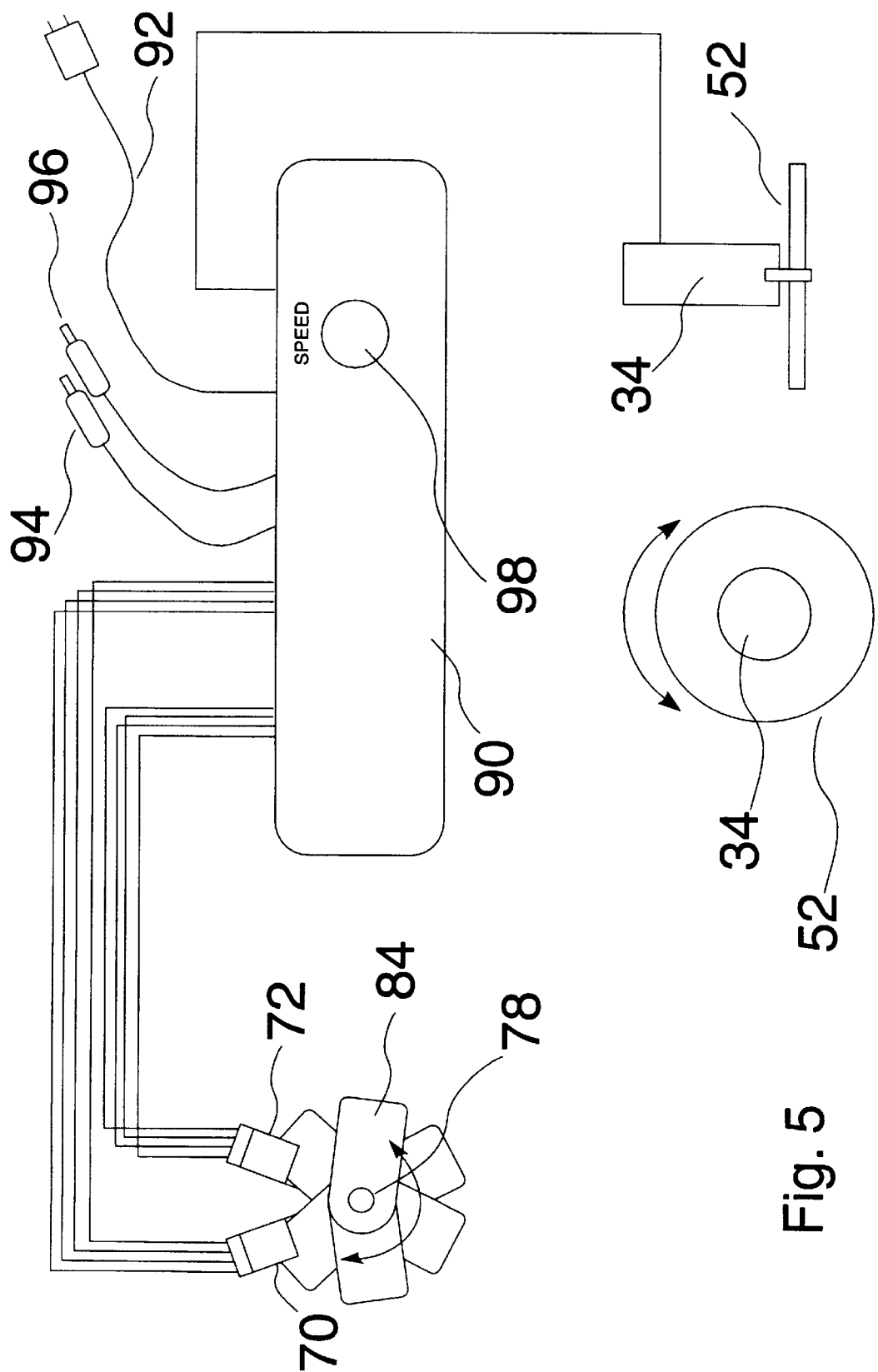
FIG. 5 shows a block diagram of the electronic components of the embodiment of FIG. 1 and FIG. 4.

Referring now to FIG. 5, there is shown a block diagram of the electronic components of the embodiment of FIG. 1 and FIG. 4. In general, the electronic components of system 10 includes first and second sensors 70 and 72, analog controller 90, and motor 34. Electric power is supplied to all components through power cord 92 to analog controller 90. Each optical sensor 70 and 72 has four wires extending therefrom and connected to analog controller 90 as illustrated. Two of such wires are used for provision of power, and two of such wires are for the activation signal of the applicable sensor 70 or 72. Analog controller 90 also includes recorder leads 94 and 96 for connection to a recorder to track the direction of rotation of the animal based on which of the optical sensors 70 or 72 is activated and the frequency of such movements. Analog controller 90 also includes speed control 98 which comprises a potentiometer for varying the power level sent to motor 34 to thereby vary the speed of rotation of motor drive wheel 52.

Referring now collectively to FIG. 1, FIG. 4 and FIG. 5, the operation of system 10 will now be described. Up and down motion of animal 12 does not result in rotation of cage 12. Rather, such vertical movement is compensated for by counterbalanced arm 38 which also moves vertically in response thereto.

If animal 12 rotates in a clockwise or counterclockwise direction in cage 14, cage 14 is caused to rotate in the counter-rotational direction in response thereto. Specifically, when animal 12 rotates, first bracket 82 is caused to rotate by the connection of tether line 26 to animal 12 and second bracket 84. Second bracket 84 is caused to rotate by rotation of hollow tube 78 about its axis of rotation and about lead bundle 66 (or leads 18, 20, 22 and 24 in FIG. 1), but without rotating lead bundle 66 or leads 18, 20, 22 and 24 in FIG. 1. Rotation of first bracket 82 also results in rotation of second bracket, or rotating element, 84. The portion of rotating element 84 capable of intersecting the light beams of first and second optical sensors 70 and 72 will eventually activate either first sensor 70 or second sensor 72 by interrupting the respective light beam emanating therefrom.

Activation of first sensor 70 or second sensor 72 results in receipt of a respective activation signal by analog controller 90. Controller 90 determines the polarity of the signal to be sent to motor 34 based on whether first sensor 70 or second sensor 72 has been activated. Controller 90 then sends the polarity signal, the amplitude of which may be adjusted by speed control 98, to motor 34 to cause motor drive wheel 52 to rotate in the desired direction and at the desired speed. Rotation of motor drive wheel 52 results in rotation of turntable 16 and cage 14 in a direction opposite of the direction of rotation of animal 12. Rotation of container 14 turns animal 12 and tether line 26, and, in turn, first bracket 82, hollow tube 78, and second bracket 84. As second bracket 84 exits sensor 70 or 72 (due to the counter-rotation of the animal by the device, or movement by the animal in a reverse direction), the respective light beam is restored and the signal to controller 90 terminates, thereby shutting down motor 34 and the movement of turntable 16.

In the embodiment of FIG. 5 with directions determined by viewing from above as in FIG. 5, if animal 12 rotates in a counterclockwise direction, rotating element 84 rotates in a counterclockwise direction thereby activating second sensor 72. Activation of second sensor 72 results in a motor signal from controller 90 having a polarity to cause drive wheel 52 of motor 34 to rotate in a counterclockwise direction. Counterclockwise rotation of drive wheel 52 causes turntable 16 and cage 14 to rotate in a clockwise direction—opposite of the direction of rotation of animal 12.

Similarly, if animal 12 rotates in a clockwise direction, rotating element 84 rotates in a clockwise direction to thereby activate first sensor 70. Activation of first sensor 70 results in a motor signal from controller 90 having a polarity to cause drive wheel 52 to rotate in a clockwise direction. Clockwise rotation of drive wheel 52 causes turntable 16 and cage 14 to rotate in a counterclockwise direction.

As previously mentioned, first and second sensors 70 and 72 are positioned at a predetermined angle with respect to each other as measured with respect to rotating element, second bracket 84. In FIG. 4 and FIG. 5, the angle illustrated is approximately 314 degrees. It will be appreciated that this angle need not specifically be set at this value, but rather, the angle does impact the sensitivity of the sensor assembly, i.e., adjustment of the angle between first and second sensors will render the system more or less responsive to rotational movement of animal 12. Specifically, if first and second sensors 70 and 72 are moved closer together (an angle smaller than 314 degrees), rotating element 84 will interrupt the light beams and activate sensor 70 and 72 more frequently thereby increasing the sensitivity of system 10 to rotational movement of animal 12. If sensors 70 and 72 are further apart (an angle larger than 314 degrees), rotating element 84 will activate sensors 70 and 72 less frequently thereby reducing the sensitivity.

If the triggering element used in the present invention is not a rotational element such as second bracket 84, but rather is linear, the limit detectors' predetermined position is measured with respect to the spacing between the activatable portions of the sensor. Still, the sensitivity of the sensing means (combination of the limit detectors and the triggering element) may be adjusted by adjusting the spacing between the limit detectors with the affect of increasing or decreasing the spacing akin to modification of the angle.

It will be appreciated by those of skill in the art that the movement-responsive system of the present invention provides for the use of continuous leads (tubing, electric lines and optic fibers) without the use of swivels or commutators. This provides for numerous advantages over the prior art including, but not limited to: (a) elimination of the need to compensate for and accommodate the extra system volume of a liquid swivel; (b) no restrictions of the number and type of electrical, fluid or optical leads used in testing; (c) no restrictions on the relative placement of different types of leads; (d) elimination of the need to compensate for the liquid travel time when a swivel is employed; (e) no cross-contamination between channels of a multi-channel liquid swivel; (f) elimination of the potential for cross-talk between electrical or optical channels on a commutator and noise or interference caused by a commutator; and (g) avoidance of the extra expense resulting from continual replacement or repair of swivels seals or commutators which experience wear during normal use.

It will also be appreciated that the present invention provides for tracking of the rotational behavior of the animal. Such tracking is a general indicator of the activity of the subject animal and specific indicator of the neurochemical changes that may be occurring to the animal during testing, and therefore can be very valuable to a researcher.

It will be further appreciated that the present invention provides an apparatus whereby no unwanted stress is placed on the lead. In some prior art systems, an actual lead is used to move a physical portion of the apparatus which places stress on the lead, and which can harm the animal or result in disconnection of the lead from the animal or to the external device to which the lead is connected.

It will be appreciated that the sensor system of the present invention has the capability to be adjusted for sensitivity to the animal's movement by both physical adjustment of the angle (predetermined position) between sensors 70 and 72 and by control of motor 34 through adjustment of speed control 98 of controller 90. Such adjustment is not complex, and may be performed in the laboratory.

It will also be appreciated by those of skill in the art that because the limit detectors of the present invention are close-ended (i.e., they are either activated or inactivated and in which an activated detector can only be deactivated by reversal of movement of the animal), the control system is not complex and does not require use of a microcomputer or microprocessor to operate. Further, the use of close-ended limit detectors means that counter-rotation of the cage in response to rotation of the animal may be invoked in sufficient time to avoid entanglement, twisting, disconnection or clamping of the leads as results in prior art systems using open-ended sensors which may require one or more revolutions of the animal before reacting with counter-rotation.

It will be yet further appreciated that the entire cage of the present invention is rotated. This rotation is advantageous over rotation of only a portion of the cage as it avoids the possibility that bedding or other materials in the cage or the animal itself may become caught between the interface of rotating and non-rotating portions of the cage. Also, by providing a cover for the cage, the visual sensation of rotation experienced by the animal may be eliminated as visual clues external to the cage or container are blocked from view. Further, the arrangement of the cage in the system permits for the cage and animal to be easily removed from the apparatus.

Further, it will be appreciated that the present invention provides the researcher with a great deal of flexibility in the types of tests that can be performed with the apparatus. The researcher is not limited to a specific type of lead or leads or a specific number of leads. All this is accomplished with a system which is inexpensive to manufacture, repair and maintain, and which is also highly reliable during operation.

As used herein and in the claims, "biomedical test" includes, but is not limited to, infusion, electrophysiology blood monitoring, microdialysis, ultrafiltration, electrochemistry, optical fiber transmission, and behavior monitoring. Essentially, it is any test that may be performed on freely-moving animal in a laboratory environment which requires the use of one or more "leads". A "lead" includes fluid tubing; electrical line, optic fiber or other line which is connected to the animal at one end and to an external device at its other end for the purpose of transmission of fluids, light or other stimuli or transmission/receipt of electrical signals, fluids, light transmissions from devices within or on the animal or other data from within or on the animal. The "external device" to which a "lead" is connected at its other end may comprise a source, such as a source of fluid or other stimuli, or a device capable or receiving response signals, fluids, or data from the animal.

Also, as used herein and in the claims, "limit detector" means a close-ended sensor which is activated by means such as interruption or reflection of a light beam, magnetic field, radiation field, a flow of air or liquid, or a simple contact with a microswitch, pressure sensitive button, magnet, electrical contact wire, or other mechanism. The "triggering element" may comprise the rotatable element disclosed in the Figures, or any other means of triggering such a limit detector in accordance with the limit detector's activation mechanism and in response to rotational movement of the animal. The angle or spacing between the limit detectors is determined by the angle between or the spacing between (for a non-rotational triggering element) the "primary sensing axis" of the limit detectors, such as the positional axis of optical sensors 70 and 72, as measured in relation to the type of triggering element, i.e., rotational, linear, etc. Thus, in respect to the type of movement of triggering element, the limit detectors are in a predetermined relative position with respect to each other. The limit detectors are thus "logically" connected to the rotating means by electrical, physical, magnetic or light contacts to cause activation and deactivation of the rotation of the cage in response to movement (rotational, or otherwise) of the triggering element.

What is claimed is:

1. An apparatus for performing at least one biomedical test on a freely-moving animal, comprising:

a container for housing the animal;

means for rotating the container, the rotating means operably connected to the container;

means for sensing rotational movement of the animal, the sensing means including first and second activatable limit detectors having a primary sensing axis, the first and second limit detectors positioned such that the primary sensing axes of the limit detectors are at a predetermined relative position with respect to each other, the first and second limit detectors logically connected to the rotating means to cause clockwise and counterclockwise movement, respectively, of the rotating means upon activation thereof, and a moveable triggering element having at least a portion thereof for activation and deactivation of the first and second limit detectors;

means for supporting the sensing means above the animal, the support means connected to the sensing means;

means for tethering the animal to the sensing means, the tether means having first and second ends, the first end connected to the animal, and the second end connected to the triggering element of the sensing means; and a first test lead for performance of at least one biomedical test, the first test lead having a first end for connection to the animal, and a second end for connection to an external device;

such that rotational movement of the animal causes movement of the tether means which in turn causes movement of the triggering element of the sensing means, and upon activation of either the first or second limit detectors by the portion of the triggering element for activation of the first and second limit detectors results in counter-rotation of the container by the rotating means by activation of the respective limit detector.

2. The apparatus of claim 1, wherein said first and second limit detectors each comprise an optical sensor having a light beam emanating therefrom and activatable upon interruption of the light beam, the first and second optical sensors positioned at a predetermined rotational angle with respect to each other, and wherein the triggering element comprises a rotatable bracket having at least a portion thereof positioned to intersect the light beams of the first and second optical sensors for activation thereof when rotated by the tethering means.

3. The apparatus of claim 1, wherein the rotating means comprises a turntable and a drive motor connected to the turntable, wherein the drive motor is electrically connected to the first and second limit detectors.

4. The apparatus of claim 1, wherein the sensing means comprises a rotatable hollow tube through which the first lead passes without causing rotation of the first lead, the tether means operatively connected to the tube for rotation of the tube, and wherein the sensing means also comprises a ball bearing surrounding the hollow tube to permit rotation of the hollow tube.

5. The apparatus of claim 4, wherein the support means comprises a counterbalanced arm connected to the ball bearing, and which permits for vertical movement of the animal.

6. The apparatus of claim 1, wherein the tether means is non-invasively connected to the animal.

7. The apparatus of claim 1, wherein the tether means comprises a wire having at its first end a clamp for connection of the wire to a collar fastened to the animal.

8. The apparatus of claim 1, wherein the first test lead comprises tubing for transferring fluid the length thereof.

9. The apparatus of claim 1, wherein the first test lead comprises an electric line for transmitting electrical signals therethrough.

10. The apparatus of claim 1, wherein the first test lead comprises an optical fiber for transmitting light therethrough.

11. The apparatus of claim 1, further comprising:
a second test lead, the second lead having a first end for connection to the animal and a second end for connection to an external device.

12. The apparatus of claim 11, wherein the first lead comprises tubing for transferring fluid the length thereof, and wherein the second lead comprises an electric line for transmitting electrical signals therethrough.

13. The apparatus of claim 11, wherein the first lead comprises tubing for transferring fluid the length thereof, and wherein the second lead comprises an optical fiber for transmitting light therethrough.

14. The apparatus of claim 11, wherein the first lead comprises an electrical line for transmitting electrical signals therethrough, and wherein the second lead comprises an optical fiber for transmitting light therethrough.

15. The apparatus of claim 1, wherein the container comprises an enclosure which establishes a limit to the animal's movement.

16. The apparatus of claim 15, wherein the enclosure is comprised of translucent or transparent material to permit the animal to be viewed by an observer during operation of the apparatus.

17. The apparatus of claim 15, wherein the enclosure comprises a bottom exterior surface, an exterior wall surface, and at least one fastener affixed to the exterior wall surface, the apparatus further comprising:
a removable cover having at least one mating fastener attached thereto, the at least one mating fastener positioned for fastening with the at least one fastener of the bowl, such that substantially the entire exterior wall surface of the bowl is covered by the cover when so fastened.

18. The apparatus of claim 1, further comprising:
means for tracking both the frequency and direction of the rotational movement of the animal, the tracking means logically connected to the first and second limit detectors.

19. An apparatus for performing at least one biomedical test on a freely-moving animal, comprising:
a container for housing the animal;
means for rotating the container in response to rotational movement of the animal, including
means for sensing rotational movement of the animal, the sensing means comprising
first and second optical sensors activated upon interruption of a light beam emanating therefrom, the first and second sensors positioned such that the sensors are at a predetermined rotational angle with respect to each other as measured between the light beams, and
a rotating element having at least a portion thereof positioned to interrupt the light beams of the first and second sensors during rotation of the rotating element;
means for driving rotation of the container, the driving means electrically connected to the first and second optical sensors, such that activation of the first sensor causes the driving means to rotate the container in a clockwise direction and activation of the second sensor causes the driving means to rotate the container in a counterclockwise direction; and
means for tethering the animal to the sensing means, the tether means having first and second ends, the first end connected to the animal, and the second end connected to the rotating element of the sensing means to cause rotation of the rotating element upon rotational movement of the animal; and
at least one test lead for performance of at least one biomedical test, the lead having a first end for connection to the animal and a second end for connection to an external device,
such that rotational movement of the animal causes the rotating element of the rotating means to interrupt either the first or second sensors to thereby result in counter-rotation of the container.

20. The apparatus of claim 19, wherein the rotating means further comprises:
means for supporting the sensing means above the animal, the support means connected to the first and second sensors, and the rotating element being rotatably connected to the support means.

21. An apparatus for performing at least one biomedical test on a freely-moving animal, comprising:
a container for housing the animal;
means for rotating the container, the rotating means operably connected to the container;
means for sensing rotational movement of the animal, the sensing means including
first and second activatable limit detectors having a primary sensing axis, the first and second limit detectors positioned such that the primary sensing axes of the limit detectors are at a predetermined relative position with respect to each other, the first and second limit detectors logically connected to the rotating means to cause clockwise and counterclockwise movement, respectively, of the rotating means upon activation thereof, and a moveable triggering element having at least a portion thereof for activation and deactivation of the first and second limit detectors;

means for supporting the sensing means above the animal, the support means connected to the sensing means; and means for tethering the animal to the sensing means, the tether means having first and second ends, the first end for connection to the animal, and the second end connected to the triggering element of the sensing means, wherein the tether means comprises a first test lead for performance of at least one biomedical test;

such that rotational movement of the animal causes movement of the tether means which in turn causes movement of the triggering element of the sensing means, and upon activation of either the first or second limit detectors by the portion of the triggering element for activation of the first and second limit detectors results in counter-rotation of the container by the rotating means by activation of the respective limit detector and recording of the direction of rotation by a recording device electrically connected to the controller which in turn is electrically connected to the limit detector.

\* \* \* \* \*